United States Patent [19]
Crisio

[11] Patent Number: 5,513,989
[45] Date of Patent: May 7, 1996

[54] DENTAL IMPLANT SADDLE STABILIZER

[76] Inventor: Raymond A. Crisio, 18 S. 13th St., Belleville, Ill. 62220

[21] Appl. No.: 222,061

[22] Filed: Apr. 4, 1994

Related U.S. Application Data

[63] Continuation-in-part of Ser. No. 69,335, Jun. 1, 1993, Pat. No. 5,302,127.

[51] Int. Cl.⁶ .................................................. A61C 8/00
[52] U.S. Cl. .......................................... 433/176; 433/173
[58] Field of Search .................................. 433/173, 174, 433/175, 176, 201.1

[56] References Cited

U.S. PATENT DOCUMENTS

| | | | |
|---|---|---|---|
| 4,359,318 | 11/1982 | Gittleman | 433/173 |
| 4,379,694 | 4/1983 | Riess | 433/201.1 |
| 4,511,336 | 4/1985 | Hidaka et al. | 433/173 |
| 4,702,697 | 10/1987 | Linkow | 433/176 |
| 5,201,736 | 4/1993 | Strauss | 433/174 |
| 5,209,659 | 5/1993 | Friedman et al. | 433/173 |

*Primary Examiner*—John J. Wilson
*Attorney, Agent, or Firm*—Robert K. Rhea

[57] ABSTRACT

A stress stabilizer for a dental implant is formed by an inverted substantially U-shaped saddle for straddling an intermediate portion of an alveolar ridge of a mandible in contiguous contact with cortical bone. The bight portion of the U-shape is bored and counterbored from respective ends of the bore for alignedly guiding prosthesis components secured together through the saddle bore by a pin.

4 Claims, 2 Drawing Sheets

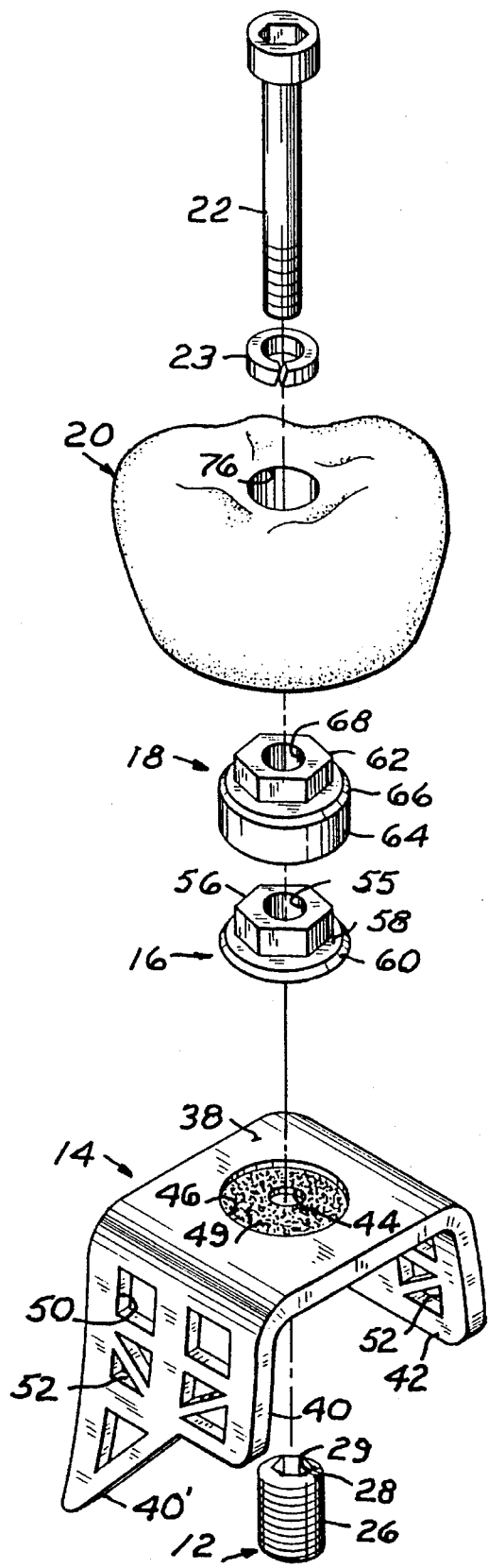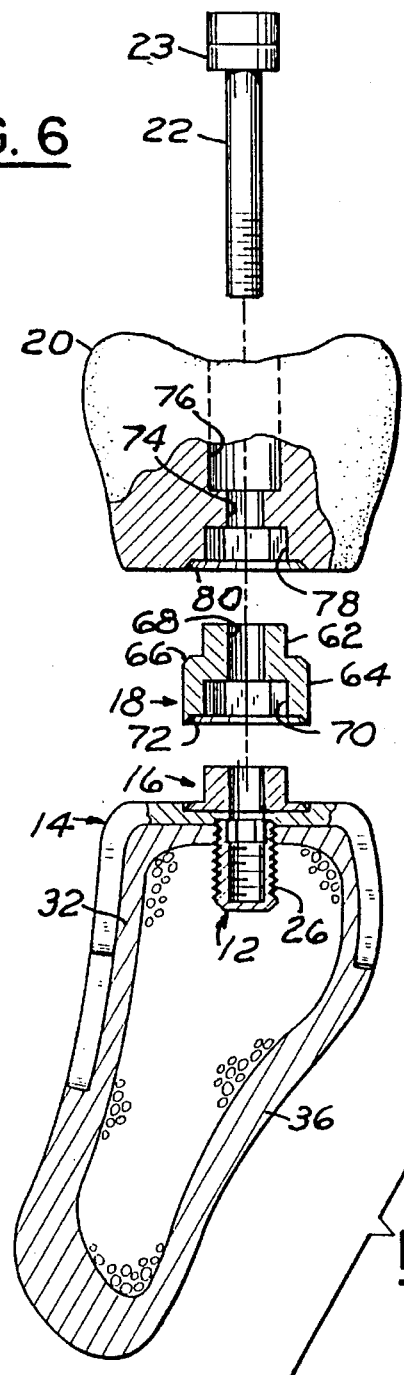

DENTAL IMPLANT SADDLE STABILIZER

This application is a continuation-in-part of an application filed by me in the United States Patent and Trademark Office on Jun. 1, 1993 under Ser. No. 08/069,335 for DENTAL IMPLANT STRESS STABILIZER, now U.S. Pat. No. 5,302,127 and included herein by reference.

BACKGROUND OF THE INVENTION

This invention relates to dentistry and more particularly to a dental implant having a saddle-type stabilizer to increase distribution of implant stresses to a larger area of the cortical plate.

1. Field of the Invention

Dental prosthesis formed of selected material are conventionally implanted and anchored in place by mechanical means such as pegs.

The use of allografts and autographs in guided tissue regeneration has greatly increased the use and market of dental implants. However, bone can only withstand a certain amount of stress before it fails. In current implant designs, it is believed unlikely that a single molar implant can serve for extended use with the root tip anchored in medullary (spongy) bone.

This invention spreads the sheer stresses from an implant throughout more cortical plate area than conventional single cylinder dental prosthesis.

2. Description of the Prior Art

U.S. Pat. No. 4,511,336 issued Apr. 16, 1985 to Hidaka et al for ARTIFICIAL APPETITE DENTAL ROOT discloses a generally cylindrical dental implant having a generally hexagonal-shaped step diameter inwardly projecting end portion in which the larger diameter portions are wedged against a solid bone portion of the jaw to provide circumferential spaces around the reduced diameter portions between the larger diameter portions for inducing osseous labrinth bone growth.

U.S. Pat. No. 4,359,318 issued Nov. 16, 1982 to Gittleman for DENTAL IMPLANT discloses anchoring a dental implant by using a drill bit similar to a hole saw for forming an annular socket in the osseous bone around a centrally bored upstanding stump for receiving a complimentary sized foraminated annular wall implant. An electrode is mounted in the stump bore and connected with a battery to apply electrical current to the electrode and induce bone apposition in the stump and bone tissue to knit through wall apertures in the sleeve implant.

This invention is distinctive over these patents by an implant fitted in either an extraction site, with or without the loss of the buccal/lingual cortical plate, a drilled bore hole, or an ailing implant.

SUMMARY OF THE INVENTION

The cortical plate has a titanium contoured saddle of continuous truss design at a bridge center pier abutment fused into the compact bone. By fusion this contoured saddle is partially to completely imbedded in the thicker cortical plate of the jaw bone. This thicker cortical plate lies buccal and inferior in the body of the mandible and lingually in the maxilla and palatal cortical plates. The saddle spreads stress into the jaw bone away from shorter molar implants, thus preventing trauma at the saddle bone interface preventing an overload and eventually a failed implant.

With the masticating musculature attaching to the posterior portion of the mandible the flexion is greater anteriorly than the posterior mandible. Therefore, it's feasible to maintain permanent anchorage on the distal of an implant than the mesial. This saddle is designed to have a stress relief feature which allows for mandibular flexion. The shortened mesial portion of the saddle acts as a relief valve and allows the mesial portion to dislocate while the distal saddle and a cylindrical implant maintain anchorage.

The distal anchorage maintains stability and allows the mesial saddle to repair by primary bone healing (contact healing). Contact bone healing is the proliferation of the haversian system across the fracture site. Remodeling proceeds across the immobilized fracture ends and healing takes place by bony union.

The principal object of this invention is to provide an implant support which will increase the distribution of stresses throughout more cortical plate than conventional single cylinder fixtures by spreading the horizontal and shear stress away from ankylose implants to maintain a healthy osseointegrated interface between the support and bone by preventing a stress overload and enhancing longevity of an implant.

BRIEF DESCRIPTION OF THE DRAWINGS

FIG. 6 is an exploded perspective view of the prosthesis components; and,

FIG. 7 is a partially exploded perspective and vertical cross section view partially in elevation.

DESCRIPTION OF THE PREFERRED EMBODIMENTS

Figure 1:
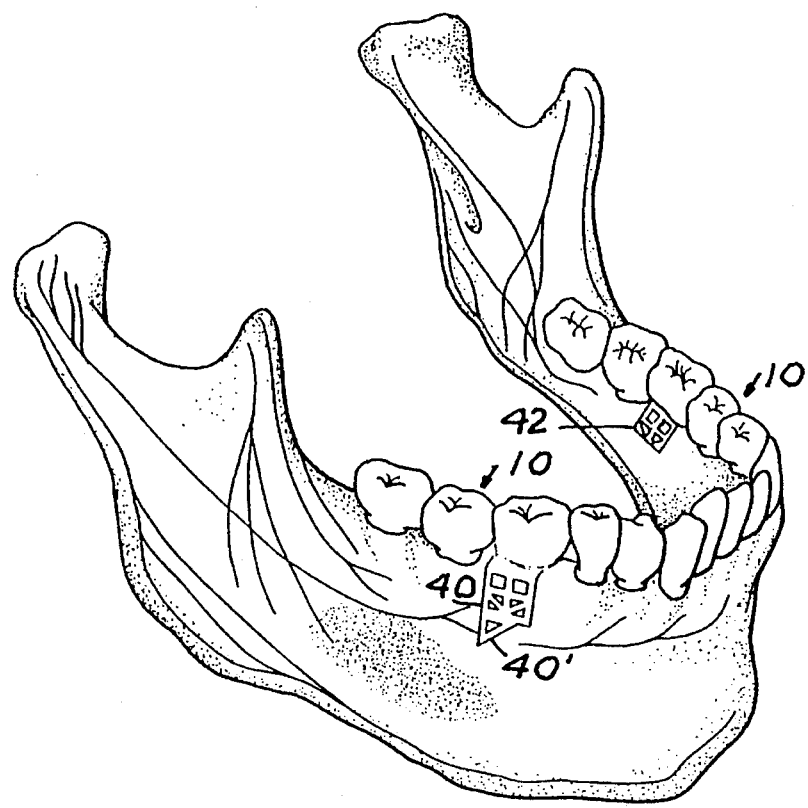
FIG. 1 is a perspective view of a lower mandible illustrating the device when installed.
Figure 2:
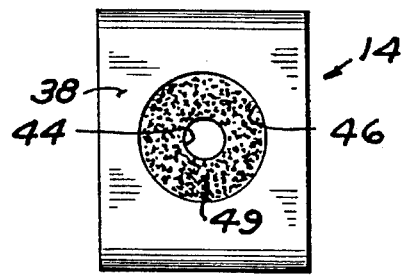
FIG. 2 is a top view of an implant supporting saddle.
Figure 3:
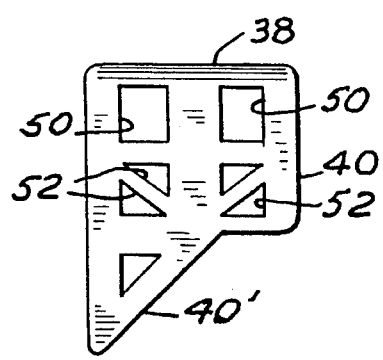
FIG. 3 is a front side elevational view of FIG. 2.

Like characters of reference designate like parts in those figures of the drawings in which they occur.

In the drawings:

Referring first to FIGS. 1, 6, and 7 the reference numeral 10 indicates the prosthesis as a whole comprising an anchor or implant 12, a saddle 14, a guide or locator 16, an abutment 18, a tooth 20, and a stud bolt-type connecting pin 22.

The implant 12 is sleeve-like having one open end and external and internal threads 24 and 26, respectively, and characterized by a 45° outer periphery 28 at its open top end for the purposes presently explained. The outer cylindrical surface of the implant 12 may be smooth, if desired. The inner periphery of its upper end portion is provided with hexagonal wrench flats 29 for the purpose presently explained. The implant 12 is threadly inserted into a hole 30 formed through the alveolar ridge of the cortical plate 32 into the medullary bone 34 of a mandible 36 by an Allen wrench, not shown, or the like.

The implant 12 (FIG. 5) is relatively small, for example, 3 mm outside diameter by 4 mm in length for minimal disturbance of the medullary bone.

Referring also to the remaining Figs., the saddle 14 is strap-like inverted U-shape in general configuration having a coronal bight portion 38 and depending legs 40 and 42 with the leg 40 projecting downwardly beyond the limit of leg 42 in a triangular shape 40'. The spacing between the legs 40 and 42 at their juncture with its bight portion 38 is dimensioned to closely envelop respective sides of the alveolar ridge which gives longitudinal support to the prosthesis during mastication.

Figure 4:
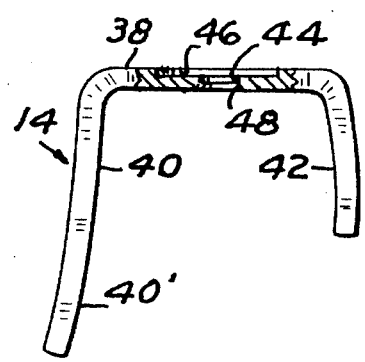
FIG. 4 is a right side elevational view of FIG. 3.
Figure 5:
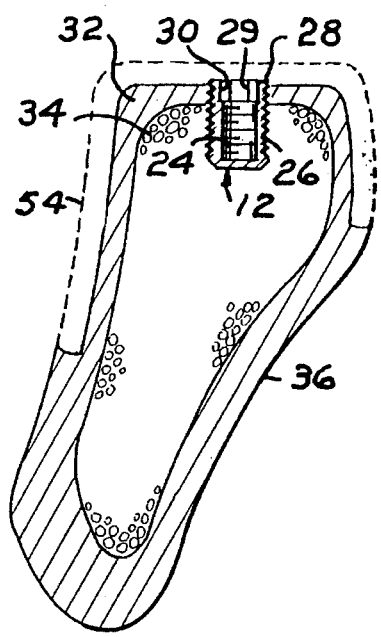
FIG. 5 is a vertical cross sectional view of a mandible illustrating by dotted lines a removed portion of the cortical plate.

The legs 40 and 42 are arcuately curved to the left, as viewed in FIGS. 4 and 5, for cooperative contact with the cortical bone 32 on the lingual and mesial sides, respectively, of the mandible.

The bight portion 38 is centrally, drilled as at 44 for axial registration with the implant 12 and is counterbored from each end, as at 46 and 48 (FIG. 4), for the reasons presently explained. The upwardly facing surface of the counterbore 46 surrounding the bore 44 is roughened or matted, as at 49, for the purpose presently explained.

Each of the saddle legs 40 and 42 are provided with a plurality of rectangular and triangular shaped openings 50 and 52 which allows a clinician adequate viewing of a periapical radiograph.

The saddle 14 is fitted over the alveolar ridge in contact with and imbedded in the cortical bone 30 by grinding off a layer of the cortical bone in that area indicated between the dotted line 54 and the sectioned bone of FIG. 5.

The locator or guide 16 comprises a sleeve having a smooth bore 55, a hexagonal periphery 56 and a relatively thin outstanding flange 58 at its depending end, as viewed in the drawings, defining a beveled upwardly facing peripheral edge 60 preferably formed on an angle of 45° for the purposes presently explained. The perimeter of the flange 58 is closely received by the saddle counterbore 46. The depending surface of the flange 58 is similarly roughened or matted, not shown, around the bore 55 for cooperative locking engagement with the matted surface 49 and precluding angular rotation of the guide 16 relative to the saddle 14 for the reason presently believed obvious.

The adapter or abutment 18 is external and internal step diameter sleeve-like in general configuration having a hexagonal top end portion 62 shape, as viewed in the drawings and a cylindrical depending end portion 64 of larger diameter than the perimeter of the hexagonal end portion 62 defining an upwardly converging tapered perimeter edge 66, preferably formed on a 45° angle. The sleeve bore 68 is formed on a diameter substantially equal with the smooth bore 55 of the guide 56 and the diametrically larger interior of its cylindrical portion 64 is defined by a hexagonal inner periphery 70 receiving the hexagonal end 56 of the guide 16 when placed thereover.

The depending wall surface of the cylindrical end portion 64 is counterbored to form a 45° beveled surface 72 which cooperatively nests the beveled surface 60 of the guide flange 58.

The tooth 20 is molded in a conventional fashion having a central bore 74 and upper and lower counterbores 76, 78 and 80, respectively. The counterbore 80 having a 45° inner periphery. The counterbore 78 having an inner hexagonal periphery snugly receiving the hexagonal top portion 62 of the abutment 18. The beveled surface of the counterbore 80 nests the abutment surface 66.

After inserting the stud bolt pin 22 and its lock washer 23 through the tooth 20, the abutment 18 and guide 16 it is threadedly tightened in the implant 12.

Installation Procedure

Take a measuring panorex radiograph.

Reflect gingival tissue and take two impressions of the coronal portion of the alveolar ridge above the visible undercuts planned to utilize. Double pour each impression (one for a backup).

Establish the location and angulation of the implant 12 to best suit tooth location.

Survey the diagnostic cast by lining the surveyor with the long axis of the implant. Mark the height of contour of the jaw bone.

Build a stent on the master cast to include guide pins.

The diagnostic cast will have the mesial, and distal implant limits drawn on it. The saddle 14 rests passively on the implant with its buccal and lingual limits coronal to the jaw bone height of contour.

Utilizing the stent drill a pilot hole and the implant hole in the master cast. A transfer implant is superglued in the hole in the master cast to mark the position of the implant in the jaw bone and where the saddle will seat on the implant.

With the saddle 14 and implant 12 on hand reflect the tissue, place the stent on the jaw bone and drill a pilot hole and the hole for the implant 12 and insert it to the correct depth. The contoured saddle 14 is placed on the implant and areas of cortical plate 32 are relieved until the saddle is seated passively on the implant. Slide a thin titanium wire, not shown, between the jaw bone and implant to ensure the saddle is resting entirely on the cylinder implant.

Take a periapical radiograph to ensure complete seating of the contoured saddle on the cylinder implant.

Fill in the voids under and around the contoured saddle region with freeze dried bone, not shown, to ensure complete coverage of the titanium saddle. Use the guided tissue regeneration technique on the implant.

Obviously the invention is susceptible to changes or alterations without defeating its practicability. Therefore, I do not wish to be confined to the preferred embodiment shown in the drawings and described herein.

I claim:

1. A dental implant stabilizer, comprising:

a sleeve implant for vertically entering an opening formed in the alveolar ridge of a mandible;

saddle means including a strap-like inverted substantially U-shaped saddle having a centrally bored bight portion counterbored from each end of the central bore and having depending legs for overlying the implant and straddling an intermediate portion of the alveolar ridge in contiguous contact with cortical bone and seated on said implant; and, prothesis means including a guide received by the counterbore opposite the implant and connected with the implant and supported by the saddle means.

2. The stabilizer according to claim 1 in which the prosthesis means includes:

a tooth disposed on said saddle and having an aperture axially aligned with the saddle bore; and, pin means for securing the tooth to said implant.

3. The stabilizer according to claim 2 in which the prosthesis further includes:

a centrally apertured step diameter sleeve-like abutment interposed between said tooth and said guide.

4. A dental implant stabilizer, comprising:
- a sleeve implant for vertically entering an opening formed in the alveolar ridge of a mandible;
- guide means including a strap-like inverted substantially U-shaped saddle having a centrally bored bight portion and depending legs for overlying the implant and straddling an intermediate portion of the alveolar ridge in contiguous contact with cortical bone; and,
- prothesis means connected with the implant and supported by the saddle means;
- said prothesis means including:
  - a tooth disposed on said saddle and having an aperture axially aligned with the saddle bore,
  - pin means for securing the tooth to said implant,
  - a centrally apertured step diameter sleeve-like abutment interposed between said tooth and said saddle, and,
  - a centrally bored guide having a top portion nested by the abutment and having an outstanding annular flange overlying the saddle bight portion,
- the saddle bore being counterbored from each end for nesting the adjacent end portion of said implant and the guide flange, respectively.

* * * * *